(12) United States Patent
McGill et al.

(10) Patent No.: US 8,421,017 B2
(45) Date of Patent: *Apr. 16, 2013

(54) ANALYTE DETECTION WITH INFRARED LIGHT

(75) Inventors: R Andrew McGill, Lorton, VA (US); Graham K Hubler, Highland, MD (US); Michael Papantonakis, Washington, DC (US); James S Horwitz, Fairfax, VA (US); Chris Kendziora, Burke, VA (US); Robert Furstenberg, Largo, MD (US)

(73) Assignee: The United States of America, as represented by the Secretary of the Navy, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 13/107,831

(22) Filed: May 13, 2011

(65) Prior Publication Data

US 2011/0271738 A1    Nov. 10, 2011

Related U.S. Application Data

(63) Continuation-in-part of application No. 12/255,103, filed on Oct. 21, 2008, now Pat. No. 8,101,915.

(60) Provisional application No. 61/334,922, filed on May 14, 2010, provisional application No. 61/479,871, filed on Apr. 28, 2011.

(51) Int. Cl.
*G01N 21/00* (2006.01)

(52) U.S. Cl.
USPC ........................................... 250/338.5

(58) Field of Classification Search ..... 250/338.1–338.5
See application file for complete search history.

(56) References Cited

U.S. PATENT DOCUMENTS

| | | | | |
|---|---|---|---|---|
| 5,592,170 A * | 1/1997 | Price et al. | ....................... | 342/22 |
| 6,853,452 B1 * | 2/2005 | Laufer | .......................... | 356/436 |
| 6,995,846 B2 * | 2/2006 | Kalayeh et al. | ................ | 356/437 |
| 7,800,527 B2 * | 9/2010 | Douglass et al. | ................ | 342/22 |
| 2002/0166969 A1 * | 11/2002 | Chou et al. | ............... | 250/339.08 |
| 2005/0059162 A1 * | 3/2005 | Wohleb | ......................... | 436/177 |
| 2005/0207943 A1 * | 9/2005 | Puzey | ......................... | 422/82.05 |
| 2006/0023211 A1 * | 2/2006 | Gandhi et al. | ................. | 356/318 |
| 2008/0151082 A1 * | 6/2008 | Chan | ............................. | 348/246 |

* cited by examiner

*Primary Examiner* — Kiho Kim
(74) *Attorney, Agent, or Firm* — Amy L. Ressing; Rebecca L. Forman

(57) ABSTRACT

A method for non-contact analyte detection by selectively exciting one or more analytes of interest using an IR source optionally operated to produce pulses of light and tuned to at least one specific absorption band without significantly decomposing organic analytes and determining if the analyte is present by comparing emitted photons with an IR detector signal collected one or more times before, during, or after, exciting the analyte. Another embodiment of the present invention provides a method for non-contact analyte detection by selectively exciting analytes of interest using one or more IR sources that are optionally operated to produce pulses of light and tuned to at least one specific wavelength without significantly decomposing organic analytes, wherein the analyte is excited sufficiently to increase the amount of analyte in the gas phase, and wherein the content of the gas is examined to detect the presence of the analyte.

45 Claims, 18 Drawing Sheets

(a) (b) (c)

ANALYTE DETECTION WITH INFRARED LIGHT

PRIORITY CLAIM

The present invention is a continuation-in-part application of U.S. application Ser. No. 12/255,103 filed on Oct. 21, 2008 by R. Andrew McGill et al. entitled "Detection of Chemicals with Infrared Light," the entire contents of which is incorporated herein by reference. The present application claims priority from U.S. Provisional Application No. 61/334,922 filed on May 14, 2010 by R. Andrew McGill et al., entitled "Method of Chemical or Biochemical Detection," and from U.S. Provisional Application No. 61/479,871 filed on Apr. 28, 2011 by R. Andrew McGill et al., entitled "Method of Chemical or Biochemical Detection," the entire contents of each are incorporated herein by reference.

BACKGROUND OF THE INVENTION

1. Field of the Invention

The present invention relates generally to chemical or biochemical detection and more specifically to molecular, ion pair, or ion detection by selective thermal heating with incident infrared light resonant with one or more selected infrared absorption bands, and examination of gaseous analyte or light produced as a result of said incident light.

2. Description of the Prior Art

Low vapor pressure analytes, in their condensed physical state, such as explosives, drugs of abuse, and chemical warfare agents, are often difficult to detect in a non contact or stand-off mode using conventional technology. Since the handling of these materials may leave persistent trace contaminations on contacted surfaces (e.g., door handles, pockets, hands, containers, etc.), manual swipes are often used to lift particles or residue of the analytes for subsequent analysis, for example in airport hand luggage screening. However, performing a manual swipe of each potential suspect and container is often impractical or inconvenient, and it inhibits covert detection.

A summary of existing and emerging technologies for the portable detection of contaminants, such as chemical warfare agents, is outlined by Michael W. P. Petryk in his article entitled "Promising Spectroscopic Techniques for the Portable Detection of Condensed-Phase Contaminants on Surfaces," found in *Applied Spectroscopy Reviews*, 42: 287-343, 2007, the entire contents of which are incorporated herein by reference. Moreover, U.S. Pat. No. 6,998,156 to Bubb et al. describes using an infrared laser to vaporize target material. The entire contents of the Bubb patent are incorporated herein by reference.

For trace detection of explosives or drugs, the current technologies typically work well as long as particles can be collected by some physical means and then thermally converted into a gas for analysis or detection. The sampling techniques commonly use non-selective removal of particles from a selected few surfaces which may have been contaminated with particles of explosives and transfer them onto a heated surface which is interfaced to an ion mobility spectrometer (IMS) or other explosive detection system (EDS). Previously, this has required either a physical rubbing process or forced air removal, neither of which is material selective or practical for any significant stand-off distance and can add a significant time and personnel cost burden to the detection process. In addition, the efficiency of physical removal of particles from a surface as particles depends on the techniques used, the training level of the person removing the particles, and the rubbing or contaminated surface material or surface roughness of contaminated surfaces.

Known methods of heating trace samples of explosives for detection purposes include broad band IR sources which heat in a non-selective fashion. This approach consumes much more power than a selective heating process and generally heats everything incident with the heating source. This increases the general background level in the gas phase of all the volatile chemicals in the material examined and may result in an increase in signal clutter or false alarms, especially when the substrate materials or additional contaminants being examined are of a complex natural origin such as leather, wood or food products.

Laser induced breakdown spectroscopy (LIBS) is an alternative laser based technique but this requires significantly higher power and results in the destruction of the sample of interest and the surface on which it directly resides. The lasers used for LIBS are typically high intensity ($GW/cm^2$) with short wavelengths (UV to near IR) and are not considered safe for environments where humans might be exposed or for the integrity of the substrate being examined. LIBS is a type of atomic emission spectroscopy which utilizes a highly energetic laser pulse as the excitation source to ablate material, forming a plasma containing elemental constituents. LIBS can analyze any matter regardless of its physical state, be it solid, liquid or gas. Because LIBS detects the elemental state, its selectivity in the presence of many materials is complicated by its reliance on signal ratios of elements which can be confused when mixtures of materials are present. Nitrogen, for example, is present in many explosives but it is also prevalent in cotton or wool fiber or any proteinacous material. Trace explosives present on natural fibers would be difficult to detect accurately with LIBS.

Raman spectroscopy is an emerging standard for optical identification and characterization of known and unknown samples. It couples to signature vibrational modes of the analyte and is complementary to infrared spectroscopy. Its main drawback is in its inefficiency because typically only one photon is Raman scattered for every million photons incident on the sample. Furthermore, Raman is isotropic, meaning there is no preferred direction for the scattered light to travel. This limits its application for stand-off detection. For a fixed collection optic diameter, the photon collection efficiency decreases proportional to the second power of the distance to the sample under interrogation. Finally, Raman efficiency is optimized with high photon energy light which is not eye-safe to use in the presence of people without suitable protective measures.

Photo-thermal spectroscopy is another potential tool that is used in stand-off detection. In this technique, the sample is heated with a non-resonant, not eye-safe laser (usually visible wavelength or near-IR) in a periodic fashion (using a mechanical chopper). The detected signal consists of the amplitude of the heated signal measured by an IR detector (or some other means) and its phase-angle shift with respect to laser heating. This method differs from the present invention, in part, because it does not take advantage of the resonant nature of absorption of IR radiation which allows analyte selectivity right at the excitation stage and with much less laser power to achieve suitable heating.

One method of detecting explosives uses a broadband heating source connected to an ion mobility spectrometer. One problem with this method is that the entire composition of the surface, and possibly deeper, is heated which makes accurate detection of the analyte more difficult, because interferents may also be heated and their concentration in the gas phase increased. Another method of detecting explosives, narcotics and other chemical substances uses a laser source to ablate the particles, then collects them and subsequently analyzes them. Unfortunately, the ablation process may damage the analyte, resulting in additional signal clutter and possible reduction in the principal analyte signal, and this method requires a separate analyte collection step.

BRIEF SUMMARY OF THE INVENTION

The aforementioned problems are overcome in the present invention which provides a method for non-contact analyte detection by selectively exciting one or more analytes of interest using an IR source optionally operated to produce pulses of light and tuned to at least one specific absorption band without significantly decomposing organic analytes and determining if the analyte is present by comparing emitted photons with an IR detector signal collected one or more times before, during, after, or any combination thereof exciting the analyte. Another embodiment of the present invention provides a method for non-contact analyte detection by selectively exciting one or more analytes of interest using one or more IR sources that are optionally operated to produce pulses of light and tuned to at least one specific wavelength without significantly decomposing organic analytes, wherein the analyte is excited sufficiently to increase the amount of analyte in the gas phase, and wherein the content of the gas is examined to detect the presence of the analyte. Likewise, the present invention may be applied to inorganic or ionic based analytes. However, because in most cases ion pairs are not stable in air, the heating of these analytes to high enough temperatures naturally leads to dissociative desorption and an increase in the gaseous content of the related products.

The present invention has many advantages over the prior art. It may be operated to detect at stand-off distances and be safely pointed at targets in areas with people present without the need for any protective equipment. It may selectively target materials in a complex matrix. It may simultaneously detect a range of materials (e.g., explosives, drugs, and chemical agents). It may detect at video frame rates or faster. It may be reduced to a hand held configuration that takes advantage of the miniature size of some light sources such as quantum cascade lasers and others. It may be operated without the analyzed persons being cognizant of the ongoing detection process. It may efficiently vaporize or probe particles that are embedded in a surface such that they are difficult to remove using the normal physical rubbing or particle removal techniques. It may heat analyte without imparting significant heat to the substrate or interferents also present on the substrate. It may be used equally well with mixtures of particulate analytes of varying size. It may be used equally well with particulate analytes which can cause significant glint problems with reflectivity based techniques, and characterized by variable signal intensities when viewed at slightly different angles.

For the stand-off detection of explosives and devices such as IEDs, photonic detection has several inherent advantages compared to other methods. These advantages include: an extremely high detection speed, zero interference with the existing radar and communication systems, and the potential for long range stand-off sensing. While several other all-optical techniques such as LIBS and Raman have been proposed for stand-off detection, these suffer from the fact that the wavelengths and intensities required are not safe to eyes and skin, or even to surfaces examined such as painted automobiles.

By using more than one laser (multispectral mode) or a continuously tunable laser (hyperspectral mode) further selectivity can be achieved by using a combination of resonant and/or non-resonant excitation. (For the purposes of this application, excitation means directing energy to the sample, especially shining light on the sample.) On the collection side, further selectivity can be achieved by separately detecting one or more portions of the thermal band that is characteristic to the analyte of interest. Furthermore, the present invention may use laser sources (e.g. QCLs) that are small, provide light that is invisible and may be suitably operated to be safe to the human eye or skin and are conducive to implementation in hand-held devices. Also, the transient response of the analyte to laser heating may be measured instead of a response to periodic heating, thus providing a means for rapid detection as well as circumventing the problems associated with detection of loose powders/particles (such as explosives particulate residues) that are hard to detect using photo-thermal imaging due to relatively long thermal constants. Also, the use of resonant infrared laser sources can be optionally focused to a small spot (to increase laser irradiance) to cause the analyte to partially or completely vaporize and be detected by sophisticated ion mobility spectrometer detectors or other suitable gas detectors which may be optically based and probe the gaseous analyte generated in concert with the vaporization process to allow interrogation during the time period where the concentration of gaseous analyte is high, before the gaseous analyte diffuses or moves by other means to a lower concentration condition. This embodiment of the present invention may be non-contact or stand-off, and provides advantages over currently available detection methods, especially compared to contact techniques that involve physical contact/rubbing or air jetting of the substrate to remove solid particles of material to examine.

These and other features and advantages of the invention, as well as the invention itself, will become better understood by reference to the following detailed description, appended claims, and accompanying drawings.

BRIEF DESCRIPTION OF THE DRAWINGS

FIG. 8(a) is an image with the laser off, 8(b) is an image with the laser on, and 8(c) is a differential image which clearly defines the RDX location and spatial distribution in the center.

FIG. 16 (B) is a (LWIR) infrared camera image of the automobile showing that the heating effect of the laser (light area) is minimal where no RDX is present. In FIG. 16 (C), where RDX is present, the thermal image clearly reveals the heating due to the laser (dark dot within the light area).

DETAILED DESCRIPTION OF THE INVENTION

Figure 1:
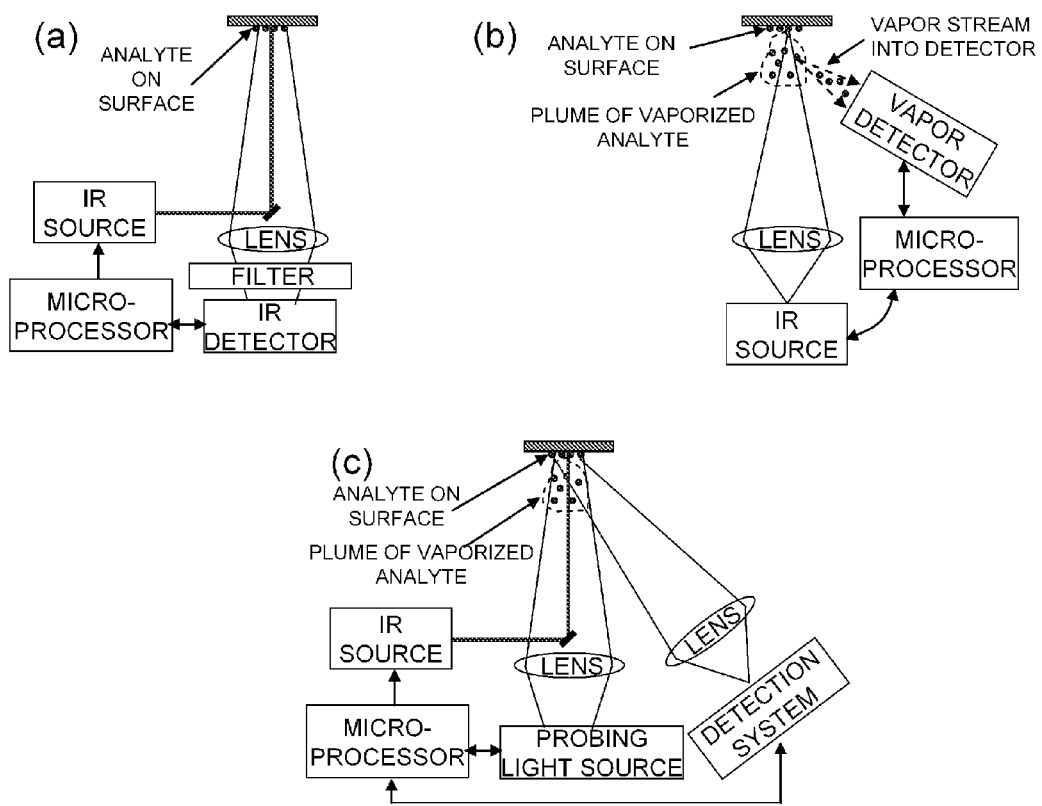
FIG. 1 is a schematic for three embodiments of the present invention: (a) shows detection using an IR source and an IR detector; (b) shows detection using an IR source and a gas detector; and (c) shows detection using an IR source, a probing light source, and a detection system.

According to the present invention, low vapor pressure analytes (e.g., explosives, additives to explosives, drugs, chemical warfare agents, biochemicals, and biological warfare agents) that are typically present as solid particles or as a thin film residue under ambient conditions can be detected at non contact or stand-off distances. After someone handles illicit materials, particles of explosives or drugs are unwittingly transferred through fingerprints onto objects and surfaces that the person touches, or after a release of a chemical or biological or radiological agent, the disseminated material is distributed onto a variety of surfaces as a trace residue. The contaminated object or surface can be excited (i.e., heated) actively and selectively by using an IR laser or a filtered light source so that a narrow wavelength range is used to be resonant with one or more selected absorption band(s) of the analyte of interest. Selective heating is used to maximize heating of the analyte of interest and to minimize heating or potential damage to materials that are not of interest to the detection application (e.g., substrate, contaminants), with the added benefit that significantly less laser power is needed. The laser is coupled in a resonant fashion to one or more selected infrared absorption band(s), with a wavelength between 1 and 20 microns, to maximize the efficiency of energy transfer and to avoid electronically excited states that commonly lead to decomposition products.

For one embodiment of the present invention, an IR laser heats trace amounts of an analyte on surfaces at stand-off distances, and the photo-thermal signal is imaged with a detector such as an IR camera. When using wavelengths corresponding to vibrational resonances specific to the trace molecules, the traces can be selectively heated and become visible in the infrared. In another embodiment of the present invention, an IR laser is used to enhance the vapor signature of the analyte thus facilitating vapor-based (e.g. ion mobility spectrometry) techniques.

Detecting the analyte of interest may be accomplished by using any appropriate analytical tool. Examples include examining thermal or photo emissions with an IR detector and examining gaseous analyte generated by the heating. (Gas is one of the primary phases of matter (along with solid and liquid) distinguished by its much lower density and much higher compressibility. For the purposes of this application, it is a more inclusive term than "vapor" in that all vapors are gas, but not all gas is a vapor.) Using thermal or photo emissions, signals, such as images, of a given object or surface are used to detect the analyte of interest. An image taken before heating is compared to an image during heating. The difference between the images or a differential image created by subtracting the image taken before from the image taken during heating can identify the presence of the analyte of interest. When sufficient laser energy is used to generate a significant amount of gas, the content of the gas can be analyzed by various optical means that are separate from the original IR heating source. This could be achieved via a light absorption phenomena or LIDAR or cavity-ringdown techniques. Alternatively, the generated gas could be analyzed by an instrument like an ion mobility spectrometer or a technique like gas chromatography.

The photo-thermal signal may be analyzed in conjunction with another optical signal such as reflectivity, emissivity, scattering, fluorescence, luminescence, Raman scattering, LIDAR, or another non-optical signal such as photo-acoustic emission. Additionally, the area to be excited with the photo-thermal probe may be selected by applying a prior cuing and/or surveying technique. The cuing or surveying technique may include reflectivity, emissivity, scattering, fluorescence, luminescence, Raman scattering, LIDAR, or photo-acoustic emission. For the purposes of this application, cuing means the use of an initial test to prompt the implementation of a second test, and surveying means the interrogation of a wide area to identify specific narrow areas for further query.

FIG. 1 shows a schematic for three embodiments of the present invention. FIG. 1(a) shows detection using an IR source and an IR detector. FIG. 1(b) shows detection using an IR source and a gas detector. FIG. 1(c) shows detection using an IR source, a probing light source, and an optical detection system.

Figure 2:
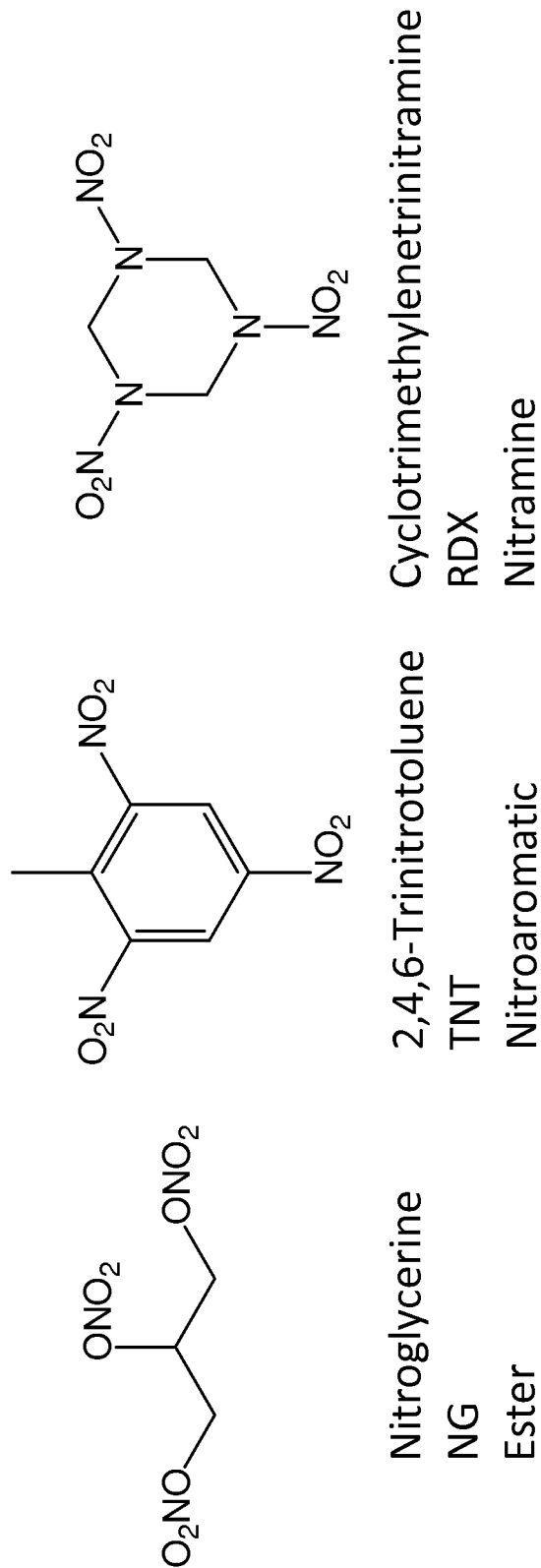
FIG. 2 shows the chemical structure of nitroglycerine, 2,4,6-Trinitrotoluene (TNT), and RDX.

The present invention provides a means to detect low vapor pressure analytes, such as explosives, drugs, and chemical agents, based on resonant absorption of certain infrared (IR) wavelengths. Some examples of explosives or components of explosives that may be detected include 24DNT, TNT, RDX, HMX, TETRYL, PETN, NG, EGDN, DMNB, ammonium nitrate, urea nitrate, ANFO, TATP, and $H_2O_2$. Some examples of drugs that may be detected include heroin, cocaine, barbiturates, LSD, and *cannabis*. Some examples of chemical agents that may be detected include nerve (G), blister (H), blood, incapacitating, and lacrymator. This system can be applied to virtually any material, including any explosive type, including organic or inorganic (ionic) explosives that cover the traditional (e.g. TNT, RDX, PETN, and ANFO) and non traditional materials (e.g. triacetonetriperoxide, or TATP, and $H_2O_2$) solid or liquid states, and it can be used to simultaneously detect all organic energetic materials probed at a common wavelength and containing the nitrogen-oxygen bond (N—O), which is in the majority of the commonly used explosives (see FIG. 2). Likewise, for the inorganic nitrates and peroxide based explosives, the system can be tuned to a wavelength at or near a peak in the absorption spectrum characteristic of the nitrate ion and peroxide structures respectively. To detect the Class A drugs, the IR source can be tuned to a wavelength at or near a peak in the absorption spectrum characteristic of the carbon-nitrogen bond. In addition to low vapor pressure analytes, the present invention is also capable of detecting higher vapor pressure analytes.

Figure 3:
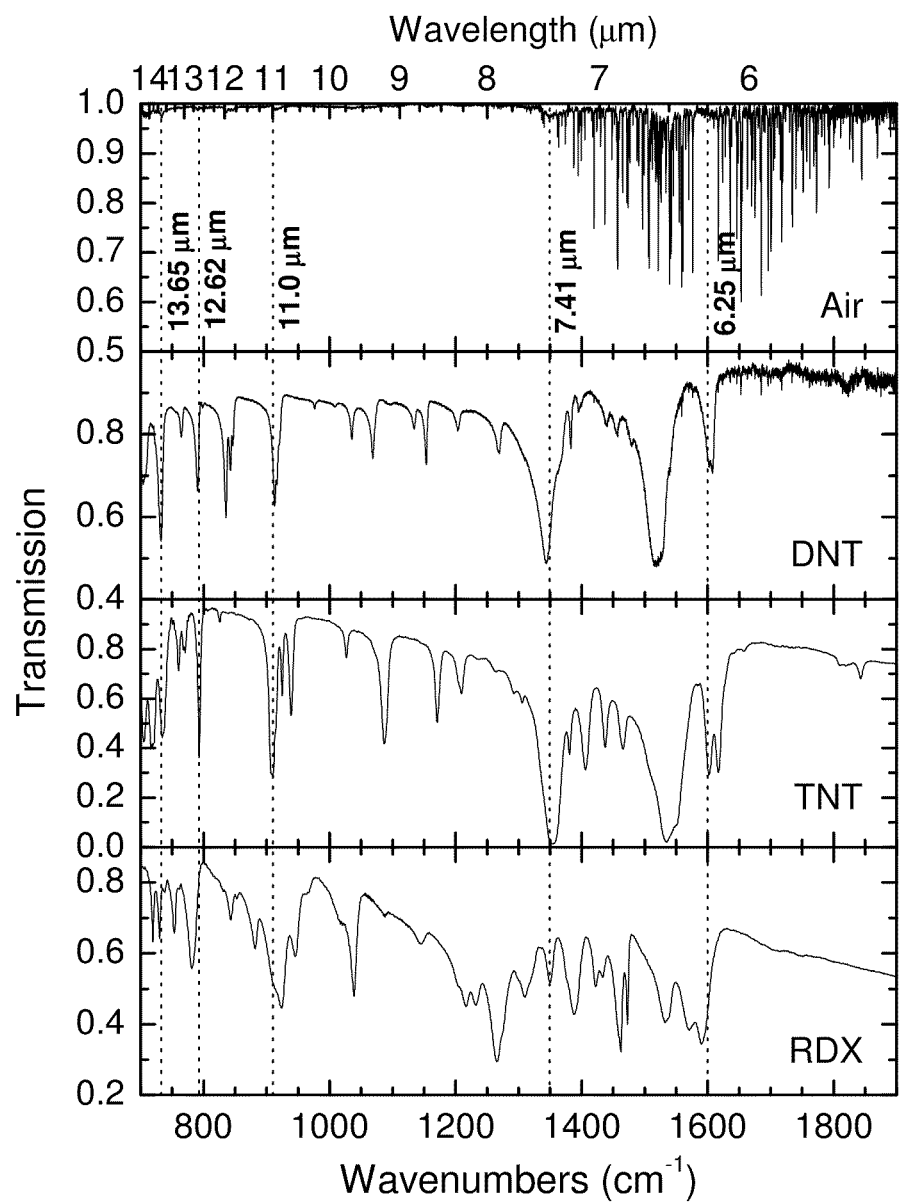
FIG. 3 shows IR transmission spectra of humid air, 2,4-dinitrotoluene (24DNT), TNT, and RDX. The N—O absorption stretching mode at 1600 $cm^{-1}$ (6.25 microns) falls in a fortuitous transparent window for air. Also highlighted are shared absorption bands at 7.41 µm, 11.0 µm, 12.62 µm and 13.65 µm that fall in an extended air transparency window.
Figure 4:
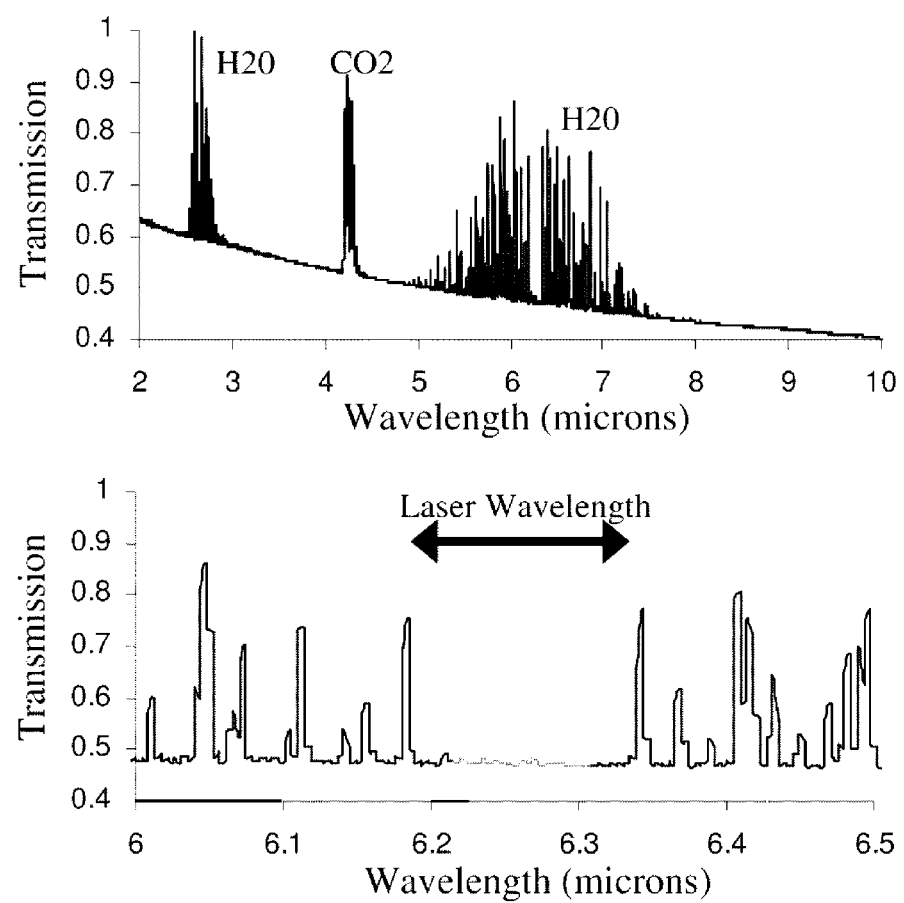
FIG. 4 shows the IR spectral absorbance properties of humidified air.

The N—O band in the nitro group has natural resonance frequencies (symmetric and anti-symmetric) in the mid and long IR wavelengths. The transmission spectra of organic-based 24DNT, TNT and RDX chemicals shows that they exhibit a common absorption band near 6.25 μm as shown in FIG. 3. This N—O stretch band and several others fortuitously fall in transmission windows of air (see FIG. 4), making them suitable for stand-off detection applications.

Because the vapor pressures of the majority of explosives are very low and typically well below a few parts per trillion at room temperature, traditional optical stand-off detection techniques applied to plumes of industrial chemicals or chemical agents are largely not useful. Additionally, the vapor pressure of explosives can be significantly reduced in composites containing explosives, such as C4, and masked due to complex packaging. However, the surface contamination of explosives and this persistence in the solid state can be exploited for stand-off or non-contact detection by irradiating the explosive sample with one or more of the resonant absorption wavelengths highlighted in FIG. 3. At these wavelengths, the coupling efficiency of the optical energy can be 1000 times greater than if the wavelength were just a few $cm^{-1}$ away. Targeting any of these absorption peaks enables rapid, selective heating of the explosive material.

As the temperature of an object increases, the amount of IR radiation it emits increases, which allows IR imaging to map out local temperature changes. Industrial, medical, and military applications make use of this technology, and, because of good atmospheric transmission at some wavelengths, remote imaging is also possible. A trace amount of explosive residue, when illuminated at a resonant IR absorption wavelength, will heat up locally and is observable by an IR camera.

If the thermal properties of the substrate on which the analyte is found are known, then the knowledge of both the degree of heating and the cooling time can be used as inputs in an alarm algorithm. For example, more heating at selected wavelengths on a metallic substrate such as a door knob (fast cooling) carries more weight (i.e. more likely to contain explosive residue) in an alarm algorithm than the same amount of heating on a plastic or fibrous substrate (slow cooling).

A time dependence of the signal may be used to distinguish emissions from the analyte and emissions from a substrate at least partially covered by the analyte. Additionally, the different times of the signal, a time dependence of the signal, or both may be used to distinguish faster emission phenomena from slower emission phenomena. Faster emission phenomena may comprise reflection, elastic backscattering, Raman scattering, or any combination thereof. Slower emission phenomena may comprise photo-thermal, photoluminescence, fluorescence, or any combination thereof. Moreover, the different times of the signal, a time dependence of the signal, or both may be used in combination with a spectral signature. For the purposes of this application, timing means the amount of time elapsed since the start of an excitation pulse, time dependence means the characteristic of a signal as a function of time since the start of an excitation pulse, temporal is a term that includes all elements of both timing and time dependence, time increments are segments into which time may be divided by a measuring device, fast refers to response phenomena from which the initial signal is detected after a relatively small (short) time increment, slow refers to response phenomena from which the initial signal is detected after a relatively large (long) time increment (fast and slow are defined only in contrast to each other—neither term implies any specific time increment), narrow (short) refers to a signal that decays in a relatively small increment of time, and wide (long) refers to a signal that persists for a relatively large increment of time (narrow and wide are defined only in contrast to each other—neither term implies any specific time increment or functional form).

Under one embodiment of the present invention, IR thermal imaging of a given scene is enhanced by illumination with an IR pulse (outside the camera detection wavelength range) to resonantly interact with the analyte or analytes of interest. By comparing images with the laser off to images with the laser on at video frame rates, a differential image with high fidelity can be generated which will distinctly identify explosive residue. For the purposes of this application, pulse means the time during which energy is directed to the sample, and pulse width means the amount of time that the energy is emitted.

Multiple illumination pulses may be used in rapid sequence. This may enhance the portion of the emitted signal emanating from the analyte surface with respect to that from the substrate or bulk. Also, the laser may be applied in two or more pulses so the first laser pulse vaporizes the more volatile components (such as but not limited to water and other potential interferents) and the second and subsequent pulses, after some pause between the pulses, will vaporize the less volatile components. The duration of laser pulses, pause between pulses, their intensity and color (i.e., wavelength) may be optimized to provide maximum separation of multi-component mixtures.

The resonant IR absorption wavelengths to use for heating should be common to explosives, but otherwise rare among possible substrate materials such as cotton, paper, plastics, metals etc. Further, by utilizing additional IR wavelengths, tests can be performed to probe for other types or classes of explosives as well as to increase system selectivity to confirm the type of explosive. In general, this approach offers advantages over other optical techniques in that it may be operated in an eye-safe and compact manner.

Thermal imaging is enhanced by the heating signature due to the resonant absorption within the explosive residues of interest. For this embodiment, powerful mid-IR laser sources and sensitive IR focal plane arrays may be used. Both of these are commercially available today and should offer increased performance in upcoming years.

The IR source may be any source known in the art, such as a pulsed laser, continuous laser, broad band light source, filtered broad band light source, swept source, chirped source, variable source, or tunable source. Preferably, a quantum cascade laser (QCL) may be used as the IR photon source. The advantages of using QCL include: It can provide a single wavelength output allowing for the targeting of specific functional groups. It can operate at room temperature, and current devices can provide up to 20 Watt CW output, and it is commercially available. Moreover, a pulse is preferred over continuous wave (CW) for higher peak power, lower laser on times, and reduced cooling requirements. It is a stable laser source which in normal operation requires no consumable materials. It is microfabricated from semiconductor wafers to generate die, in mass production, with high yield, low cost and high quality. The inexpensive and miniature nature of the QCL die is attractive for the development of hand held instrumentation. These high power output powers in a laser tunable to the absorption bands of explosives makes the QCL an enabling technology for compact detectors used in non contact or stand-off vaporization and detection of explosives.

Any thermal imaging hardware may be used. For example, an IR camera (such as a commercial FLIR camera) can be used to collect and analyze longwave infrared (LWIR) light. The advantages of this hardware include: it is a microfabricated bolometer thermal imaging array, it is uncooled for low power operation, it responds to the 7-12 µm band which includes wavelengths generated from thermal heating, and it is small and lightweight. Moreover, a telescopic lens may be used to increase stand-off distance capability.

The IR detector may be a single channel or a multi channel detector. Also, the light entering the IR detector may be filtered to be selective for the analyte of interest. Such filtering could be performed using etalon, grating, interferometer, prism, lens with chromatic aberrations, or other techniques. Such filtering could also be performed using wavelength-dependent "notch" filters, band pass filters, long wave pass filters, short wave pass filters, dichroics or other filters used in series or in parallel to extract the spectral content of the emitted light.

In accordance with Kirchhoff's law, the thermal emission spectra of analytes correlate with their absorption spectra. To take advantage of the increased emissivity levels at absorption peaks in the thermal band where the detection occurs, a suitable optical filter can be designed which passes these analyte specific wavelengths and blocks all others. This way, only a signal attributable to the analyte is collected and the signal-to-noise ratio is increased. By combining both selective excitation and selective collection, the detection limit and detection selectivity of a given analyte can be greatly increased. Moreover, one or more excitation sources may be used with one or more optical collection filters. Additionally, the excitation source, the optical collection filter or both may be tunable. A finite number of laser wavelengths may be used with one or more filters with a finite number of narrow transmission bands to increase the detection sensitivity and/or selectivity through multispectral imaging. The filters may be sequentially inserted in front of the IR detector, and a scene may be recorded for each laser pulse.

If there is sufficient IR light to generate a gaseous analyte, an optical technique may be used to examine the contents of said gaseous analyte. The analyte may be examined using an IR source, visible source, UV source, IR detector, visible detector, UV detector, diffraction grating, filter wheel, Michelson interferometer, laser cavity, integrating sphere, or any other suitable equipment. The presence of the analyte may be determined by using IR absorption, IR backscattering, IR thermal luminescence, Raman spectroscopy, LIBS, or any other suitable technique.

The collected photons may be spectrally dispersed. For example, they may be dispersed by a diffraction grating onto a single element detector, linear or 2-dimensional IR detector array. This would reduce the detector spatial dimension. In the case of a single element detector, the grating could be mechanically rotated and the narrow wavelength band the detector is exposed to would depend on the angle between the optical axis of the detector and the normal of the grating. An array detector may be used to generate a spatially resolved image of the emitted signal. Moreover, individual pixels in the same spatially resolved image may be compared to determine inhomogeneous responses, including treating some pixels as a reference for others. The IR signal may be dispersed onto a multi-channel sensor array so that the signal from individual pixels or sub groups of pixels represent distinct wavelength regions of the emission spectrum.

Malfunctioning detector pixels may be identified and managed. Bad and/or malfunctioning detector pixels may be ignored to improve detection performance. A number of frames from the IR detector/camera trained on a fixed, preferably uniform background scene can be collected. In the absence of this data, the actual data set from a detection run can be used instead. At each pixel position, the temporal output of the signal may be tested using the Anderson-Darling statistic against the hypothesis that the pixel output obeys the normal, Poisson or any other distribution found to be obeyed by the majority of the pixels. In absence of this knowledge, normal distribution can be used by default. If the ratio of the statistic at the given pixel and the average statistic for all pixels is greater than a certain predetermined value, the said pixel is considered bad and may be ignored in subsequent data processing.

Any combination of spectral signals, spatial signals, different times of the signals, and time dependence of the signals may be considered. Spectral, spatial and temporal signals may be considered for multi-component analysis algorithms to detect or identify specific chemicals. For example, the intensity on a particular pixel of an imaging array can be monitored over the time before, during and after the illumination.

In one embodiment, analyte may be trapped in a sorbent coated fiber configured for injection through an optional membrane into a chromatographic column or into an analytical system such as a mass spectrometer. The fiber may optionally include a sleeve to protect the integrity of the sorbent coated fiber which may be withdrawn to reveal the sorbent coated fiber when desired. The fiber may be coated by one or more types of sorbent material in one or more areas which may be separately bathed with light used to sequentially heat the sorbent coated areas and release analyte into an analytical system.

If gaseous analyte is generated, it can be detected by any means of detection currently available or yet to be discovered. These include ion mobility spectrometry, mass spectrometry, gas chromatography (GC), chemiluminescence, surface acoustic wave, gravimetric, microbalance, or crystal resonance. The gas may be sampled and directed to a GC column to achieve separation followed by a suitable detector for subsequent detection and analysis. The analyte may be trapped in a sorbent coated inlet region of a GC column and released by heating with IR light that enters the GC column and is incident on the sorbent coated trapping region. Also, the analyte may be trapped in a sorbent coated inlet region of a GC column and released by heating with IR light that passes through an IR transparent column material or window and onto the sorbent coated trapping region.

The gaseous analyte may be collected for subsequent analysis. The gas may be collected in a gas cell or onto a sampling coupon for storage or transportation to another location for further analysis. The gas may be directed into a preconcentrator for collection or it may be drawn into a cone or funnel that is optionally heated and then directed into a preconcentrator. After collection, the gas may subsequently be desorbed into an analytical system. For example, the gas may be directed into a micro-fabricated or other suitable preconcentrator for collection. After a sufficient collection time, the analyte in the preconcentrator may be desorbed and directed into a GC column to achieve separation followed by a suitable detector for subsequent detection and analysis. Alternatively, the gas may be directed into a preconcentrator for collection, and after a sufficient collection time, the analyte in the preconcentrator may be heated and the desorbed analyte directed to a GC column followed by a gas cell in combination with one or more IR lasers (fixed wavelength or tunable) and one or more IR detectors. By monitoring the temporal IR signal at each detector and using the expected drift time through the column for various analytes of interest, improved detection may be achieved.

The gaseous analyte may be collected onto a suitable substrate wherein the analyte is selectively excited using an IR source that is optionally operated to produce pulses of light and tuned to at least one specific absorption band and determining if the analyte is present by comparing emitted photons with an IR detector signal collected one or more times before, during, and/or after exciting the analyte. The gas may be collected to any surface suitable for spectroscopic identification. For example, the gas may be collected to a Surface Enhanced Raman Scattering (SERS) substrate and then analyzed.

An analyte on a solid surface may be released into the air by heating with an infrared source. The released analyte may then be drawn to a preconcentrator to collect analytes of interest. The preconcentrator may be subsequently heated to direct the released analyte into an analytical system (e.g. a gas chromatograph). The released analyte exiting the analytical system may enter a gas cell where the analyte is monitored and detected by using an infrared laser to excite the analyte and examining if light is produced.

The present invention can be inherently eye-safe, with anticipated IR irradiances that are far below the maximum permissible exposure limit. As such, many uses can be envisioned for this system, such as to not only scan suspected IEDs, but also to scan people (including for example: clothing, skin, glasses, shoes, hat, hair), airline boarding passes, vehicles, luggage, parcels, etc. Anything that a person handling explosives contacts is a suitable target. The analyte to be excited may be on any body part including hair and nails. The analyte may be on a piece of apparel, footwear, or accessory. The analyte may be in or on a package, baggage, a document, an electronic device, a building part, a vehicle part, or a drug.

The excitation may be directed at a grazing angle with respect to the substrate and optionally the electric field of the IR source may be parallel to the substrate. By doing so, the reflectance of the substrate is increased and substrate absorption (and thus heating) can be minimized while the amount of light absorbed by the analyte remains about the same. This can effectively reduce substrate heating and enhance the temperature contrast between the analyte and the substrate. In another embodiment, the excitation may be moved with respect to the substrate. For example, the excitation may be raster-scanned across the substrate while the laser beam is being pulsed (chopped). This may prevent the substrate from heating up too much. As the laser beam moves around, each particle only receives one short laser pulse, heats up and evaporates some of the material from its surface to create a puff of gaseous analyte while the substrate heating is a small fraction of the temperature rise of the analyte. By staying at the same spot, subsequent pulses would heat up the substrate to a point that it may start heating non-analyte interferent particles nearby and thus effectively remove wavelength selectivity. The speed of the rastering should be fast enough to stay ahead in time and space of the thermal diffusion wave generated at the previous spot from the previous laser pulse. Additionally, the IR source may deliver a finite number of pulses and the substrate temperature may be monitored. For example, the excitation may be raster-scanned across the substrate while the laser beam delivers a finite number of laser pulses, the number of pulses determined by remotely monitoring the temperature of the substrate and stopping the laser when the temperature reaches a predetermined value. This can prevent the substrate from overheating, even in rastering mode. In a typical operation, a laser would raster scan, dither randomly or move along a suitable path (that minimizes additive thermal effects in the substrate) continuously while the vapor is sampled by an analytical instrument (e.g. ion mobility spectrometer). The same spot may be visited multiple times by the laser during this scanning. By monitoring the substrate temperature, overheating can be prevented especially for substrates with a priori unknown thermo-physical properties.

The analyte to be excited may be harvested to a substrate. Prior to excitation, the analyte may be collected via an analyte collecting device, a portal system, a vacuum device, contact-swabbing a surface, or any combination of these.

Multiple IR wavelengths may be used to increase sensitivity and selectivity for a particular analyte of interest. The wavelengths may be used simultaneously or in sequence. Also, two or more lasers may be used to increase sensitivity and selectivity or expand the range of analytes examined. Multiple wavelengths used in on- and off-resonance modes would improve the selectivity of the system by removing false positives which may occur because sometimes broadband absorbers heat independent of wavelength. Looking at the difference between the signals for on- and off-resonance with neighboring wavelengths will help remove effects from materials which are broad band IR absorbers and prevent false positives. If the difference between the two differential signals is negligible, the analyte of interest is concluded to be not present. To compare the difference between signals on- and off-resonance, compare either the difference of the differential signals or just the difference between the on- and off-resonance raw signals. The nature of the algorithm applied could be tailored depending on the substrate material being examined.

The present invention is applicable in mobile and static applications. The laser and detector may be stationary while the target is moving. The target may be stationary while the laser and detector move. Also, the detector and laser may move while the target is also moving. For example, the laser may be trained on a target so that as the target moves, the laser and detector move to remain trained on the target.

Another alternative is to use single element photo-conductive infrared detectors (such as mercury-cadmium-telluride). The advantage of this alternative is higher sensitivity (allowing longer stand-off distances), increased detector speed (allowing faster moving objects to be scanned) and incorporation of a less expensive detector. Also, higher detector speeds will allow the probing of the thermal pulse immediately after resonant heating (sub-millisecond range) before the heat is transferred to the substrate (so called thermal luminescence regime), thus further decreasing the contribution of the substrate on the total thermal signature. This approach is likely to include a visible-light camera or visible optic with a crosshair reference in the user interface for aiming the instrument at the desired measurement target.

Example 1

A small sample of dimethylnitrobutane (DMNB) was positioned in a recessed stainless steel support inside a chamber under reduced pressure and positioned in line with a laser beam tuned to 6.45 microns. DMNB is a taggant that is added to formulation of explosives and has the same functional groups as some conventional explosives. It was selected for this experiment as a simulant or surrogate for an actual explosive but with very similar spectral properties. The laser used was a tunable free-electron laser. The operational characteristics of the laser were as follows: wavelength of 6.45 microns, 6 microsecond pulse train of 1 ps pulses at 2.8 GHz, energy density of 30-40 micro $J/cm^2$.

Figure 5:
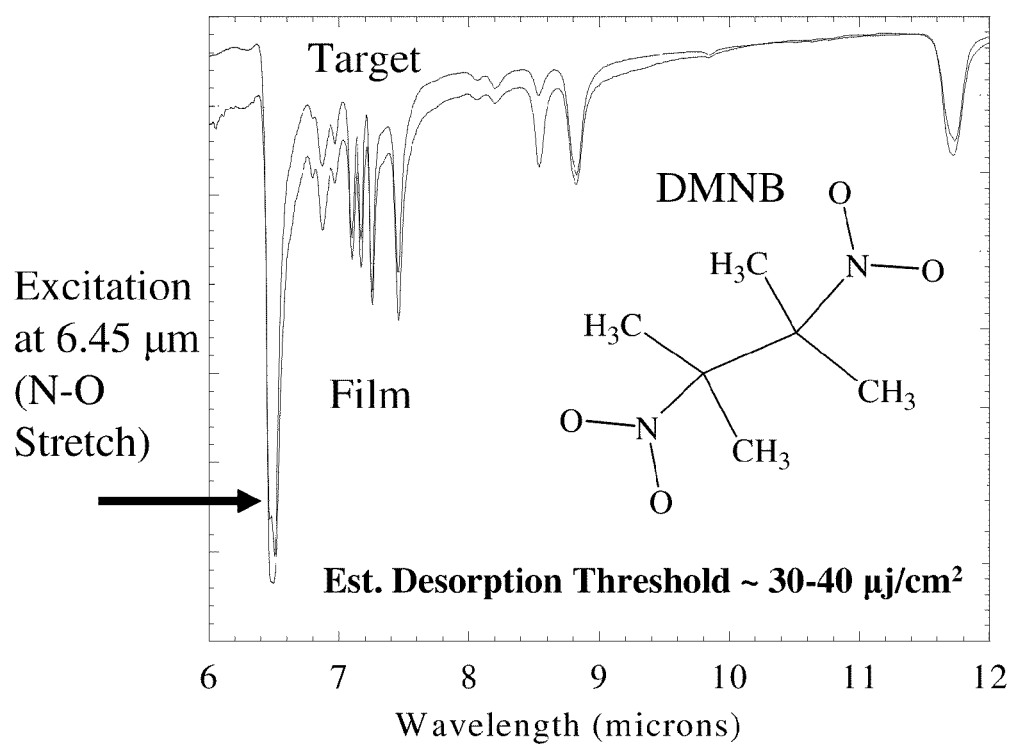
FIG. 5 shows an infrared spectrum for 2,3-dimethyl-2,3-dinitrobutane (DMNB) vaporized with an IR laser coupling to the N—O stretch. The IR laser tuned to 6.45 microns instantly evaporated the DMNB, and the collected material was shown to be essentially spectrally identical to the starting material.

Immediately after directing the laser beam onto the DMNB target a visible plume of material was ejected. Some of this material was collected on a neighboring substrate for characterization by FTIR. As shown in FIG. 5, the collected material had the same spectral signature as the starting DMNB target material, proving that the laser energy was coupled into the DMNB without any significant chemical degradation. From a visual examination of the plume and the topography of the collected material, both gas and particulate matter were ejected from the DMNB target. The laser intensity required to achieve these results was 30-40 $microJ/cm^2$.

Example 2

A small sample of 2,4-dinitrotoluene (24DNT) positioned on a test surface under ambient laboratory conditions was exposed to a laser beam tuned to 6.25 microns. 24DNT is a natural degradation product of and an impurity in TNT that is structurally very similar to TNT with one less nitro group. It was selected for this experiment as a close surrogate for TNT with very similar spectral properties which was desirable for the intended tests. The laser used was a tunable free-electron laser that allows the user to select a wide range of wavelengths.

Figure 6:
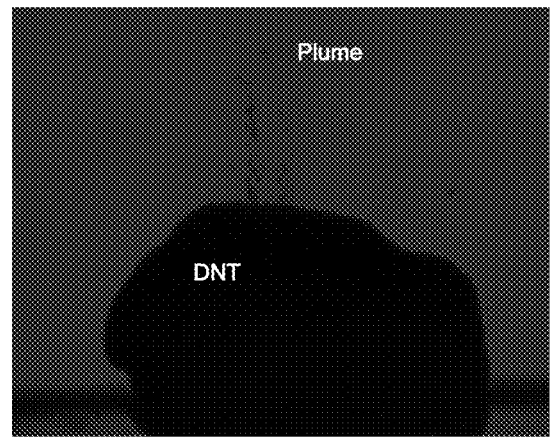
FIG. 6 shows a stroboscopic back-illuminated photo of a solid piece of 24DNT directly after exposure to a laser beam tuned to 6.25 microns. The vaporized 24DNT is clearly visible as a plume above the solid 24DNT 14 milliseconds after the laser pulse. Spectroscopic examination of 24DNT before and 24DNT after vaporization and collected on a suitable plate confirm that the 24DNT is not decomposed during the vaporization process.

The FEL tuned to 6.25 microns with 14 mJ pulses readily heated and partially vaporized the 24DNT slab (1 cm long) and 14 ms after a pulse from the laser a plume emitted is visible above the solid target. A sequence of still stroboscopic back-illuminated photos was collected in close sequence to generate a video recording the effects of the laser on the sample of 24DNT. One of the still photos is shown in FIG. 6. Some of the ejected material was collected on a neighboring substrate for further examination. Post analysis of the collected material confirmed that it had the same FTIR spectrum as the 24DNT target material. The laser energy was coupled into the 24DNT without any apparent decomposition.

Example 3

A small trace sample of RDX deposited separately on planar polyethylene and gold substrates was positioned (under ambient laboratory conditions) in line with a quantum cascade laser (QCL) beam with an output wavelength of 6.30 microns. The laser was focused to a spot size on the target of 1-2 $mm^2$. To examine any light that was emitted from the RDX sample after exposure with the QCL, an infrared camera (Photon Block 2 from FLIR, sensitive to light in the 7-12 micron range) was positioned to examine any infrared light received back from the test substrate. RDX is a common explosive in land mines and other military ordnance.

Figure 7:
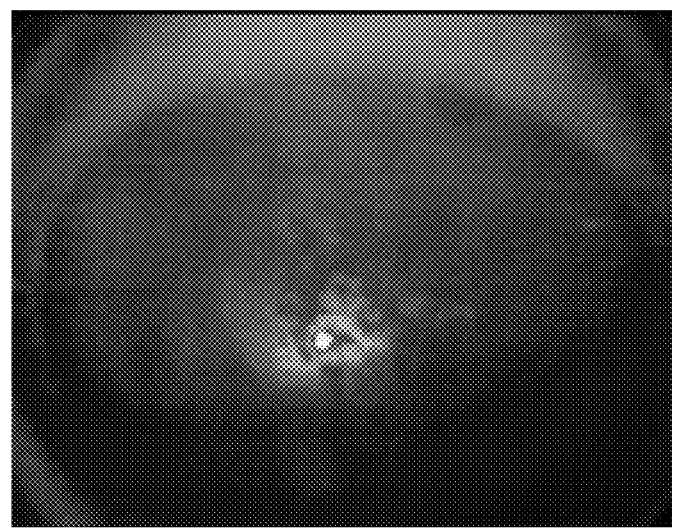
FIG. 7 is a thermal image of RDX deposited as a trace quantity on a polyethylene substrate illuminated with a QCL with incident light at 6.3 microns. The brighter area in the central part of the figure indicates the presence of the explosive.

FIG. 7 shows the thermal image of RDX deposited as a trace quantity on a polyethylene substrate, illumination with QCL at 6.3 microns (5 $mW/mm^2$). Immediately after directing the laser beam onto the RDX target, infrared light was detected indicating that the sample was being heated. When using a polyethylene substrate, the RDX heating was visible even in the background of reflected light or other emitted light. In photos taken of the sample (where black is low intensity and white is high intensity), the regions of the substrate where RDX was present appeared lighter when they were heated due to the resonant absorption of the QCL beam. Regions of the substrate where there was no RDX remained dark, indicating ambient temperature. When the laser was off, the entire region of the image was dark. Rapid RDX heating at 1 foot of stand-off is clearly seen.

Figure 8:
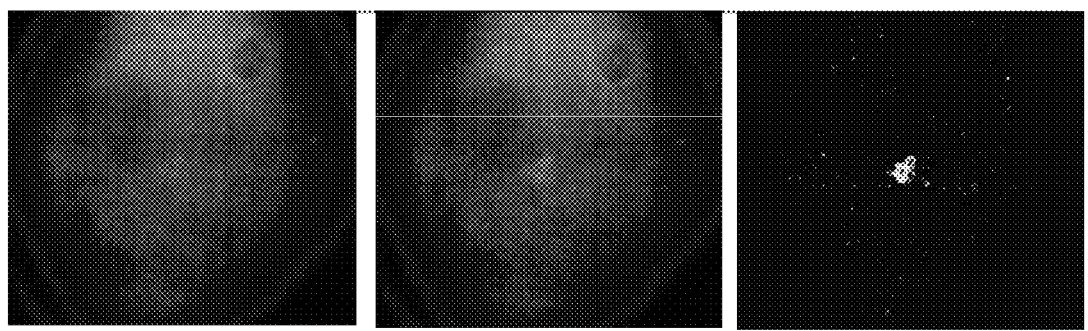
FIG. 8 shows thermal images of RDX deposited as a trace quantity on a gold minor substrate illuminated with a QCL with 5 mW/mm$^2$ incident light at 6.3 microns.

When RDX was deposited on a gold mirror, the thermal conduction away from the RDX sample was higher, resulting in less contrast between the analyte and surface. It is possible to see the thermal heating by inspection of the raw collected infrared image, but it was not as clear as the image collected on the polyethylene substrate. To enhance the image, a sequence of video frames was collected and a differential image was computed by subtracting the image directly before turning on the QCL with frames after turning on the QCL. Using this differential imaging approach, much clearer thermal image pictures were obtained to identify where the RDX was located, as shown in FIG. 8.

The above experiment was repeated with the same RDX deposited polyethylene target sample but the RDX was illuminated with a defocused spot size of 100 $mm^2$. The results of this experiment showed that the explosives were visible over a footprint range of a square centimeter.

By traversing or rastering the laser over the RDX deposited surface, the RDX could be mapped out over the entire surface examined. The QCL light at 6.3 microns efficiently coupled into the RDX sample and thermally heated the sample by a few degrees, which was sufficient to generate IR light from the RDX. The thermal image was captured with an uncooled microbolometer array IR detector (FLIR Photon Block II). The thermal heating of the RDX sample was very rapid and occurred within the time frame of the IR video used. At 30 frames/s, this indicates that significant thermal heating occurred in <30 ms. Cooling after the laser exposure ends may occur over a longer time period. The cooling rates for the RDX (and other analytes) can aid in identifying the trace explosive material.

Example 4

Figure 9:
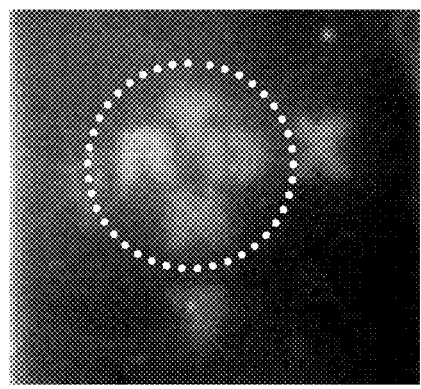
FIG. 9 shows an image of a transparent plastic substrate with RDX and TNT deposited as the horizontal and vertical letters RDX and TNT respectively and illuminated by a heat-gun but not with a laser.
Figure 10:
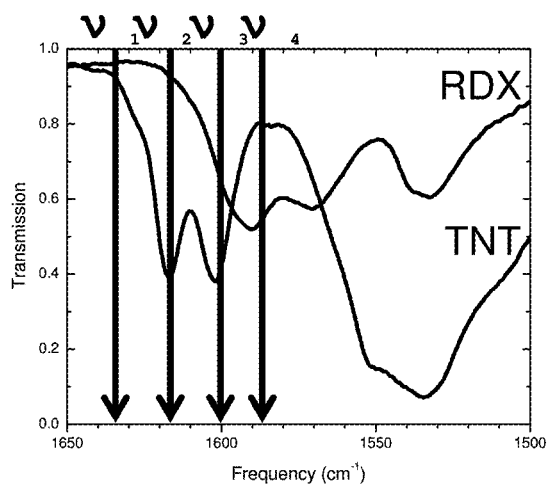
FIG. 10 shows IR transmission spectra of RDX and TNT highlighting the frequencies used in Example 4.
Figure 11:
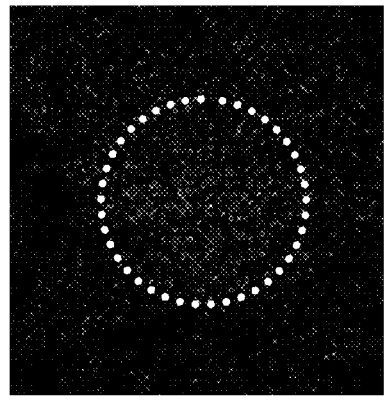
FIG. 11 shows an image of a transparent plastic substrate with RDX and TNT deposited as the horizontal and vertical letters RDX and TNT respectively and illuminated by a laser at a wavelength not selective or absorbed for either RDX or TNT.
Figure 12:
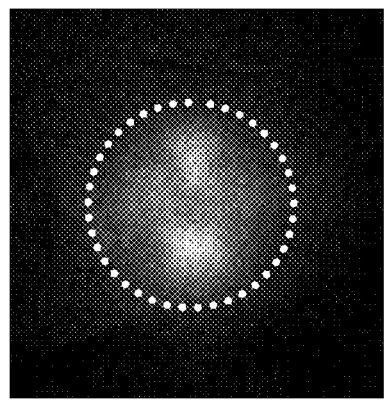
FIG. 12 shows an image of a transparent plastic substrate with RDX and TNT deposited as the horizontal and vertical letters RDX and TNT respectively and illuminated by a laser at a wavelength resonant to the TNT structure.
Figure 13:
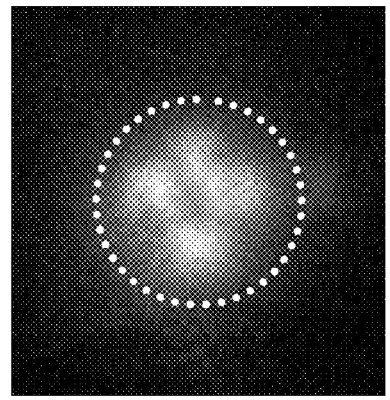
FIG. 13 shows an image of a transparent plastic substrate with RDX and TNT deposited as the horizontal and vertical letters RDX and TNT respectively and illuminated by a laser at a wavelength absorbed significantly to both the RDX and TNT structures.
Figure 14:
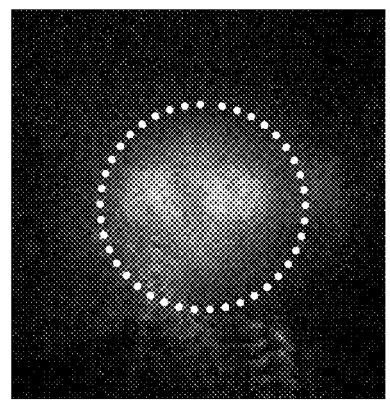
FIG. 14 shows an image of a transparent plastic substrate with RDX and TNT deposited as the horizontal and vertical letters RDX and TNT respectively and illuminated by a laser at a wavelength resonant to the RDX structure.

Selectivity was tested for a dual analyte sample containing RDX and TNT. RDX was put horizontally on a transparent plastic substrate in the form of the letters "R," "D," and "X." Similarly, TNT was put vertically on the same stainless steel surface in the form of the letters "T," "N," and "T." FIG. 9 shows the sample illuminated by a heatgun with no laser. FIG. 10 shows the frequencies that were used in the example: $v_1$ was off-resonance for both TNT and RDX, $v_2$ was on-resonance for TNT but not RDX, $v_3$ was on-resonance for both RDX and TNT, and $v_4$ was on-resonance for RDX but not TNT. As shown in FIG. 11, no image appeared when the laser was off-resonance. When on-resonance for TNT but not RDX, only the TNT letters were significantly visible (FIG. 12). When on-resonance for both RDX and TNT, both TNT and RDX letters were visible (FIG. 13). Finally, when on-resonance for RDX but not TNT, only the RDX letters were significantly visible (FIG. 14). The circles in the figures indicate the laser spot size.

Example 5

Figure 15:
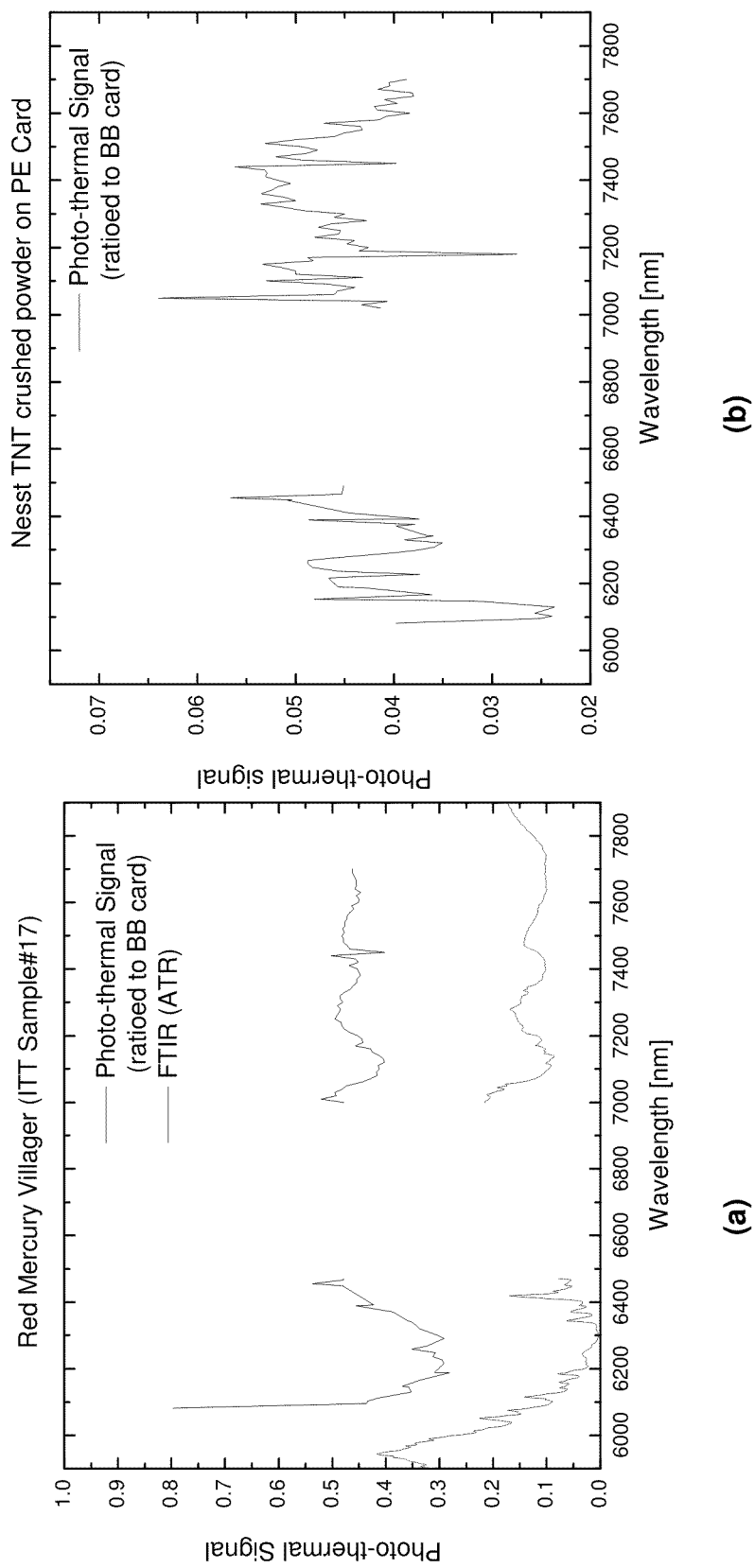
FIG. 15(a) shows the modulated (chopped at 100 Hz) signal strength as a function of excitation laser wavelength of a car panel which is an optically thick material.
FIG. 15(b) shows the modulated photothermal signal for large (>50 microns) TNT crystals.

When measuring optically thick samples or samples placed on absorbing and/or optically thick substrates, the photo-thermal signal will not exhibit strong wavelength selectivity. This is because all the wavelength of light will eventually be absorbed in a thick material. In order to recover the strong wavelength selectivity, the beam may be pulsed or chopped. This IR light modulation has the result of effectively probing the very top layer of an otherwise thick substrate. The pulsing period needs to be approximately equal or shorter that the time it takes the heat to diffuse a distance equal to the penetration depth of light at the given wavelength. This diffusion time is given by the properties of material and approximately equals $L^2/(4 A)$, where L is the penetration depth of IR light and A is the thermal diffusivity. Under these conditions, the collected photo-thermal signal strength will be proportional to the absorption coefficient of the sample. This absorption coefficient spectrum is proportional to standard FTIR spectra. FIG. 15a shows the modulated (chopped at 100 Hz) signal strength as a function of excitation laser wavelength of a car panel which is an optically thick material. The signal follows the measured FTIR reflectance spectrum. Without chopping, the spectrum would be featureless as light at all wavelengths will eventually be absorbed by the car panel. FIG. 15b shows the modulated photothermal signal for large (>50 microns) TNT crystals. The signal-to-noise is low for this sample, but the typical TNT features around 6.25 and 7.4 microns are visible.

Example 6

Figure 16:
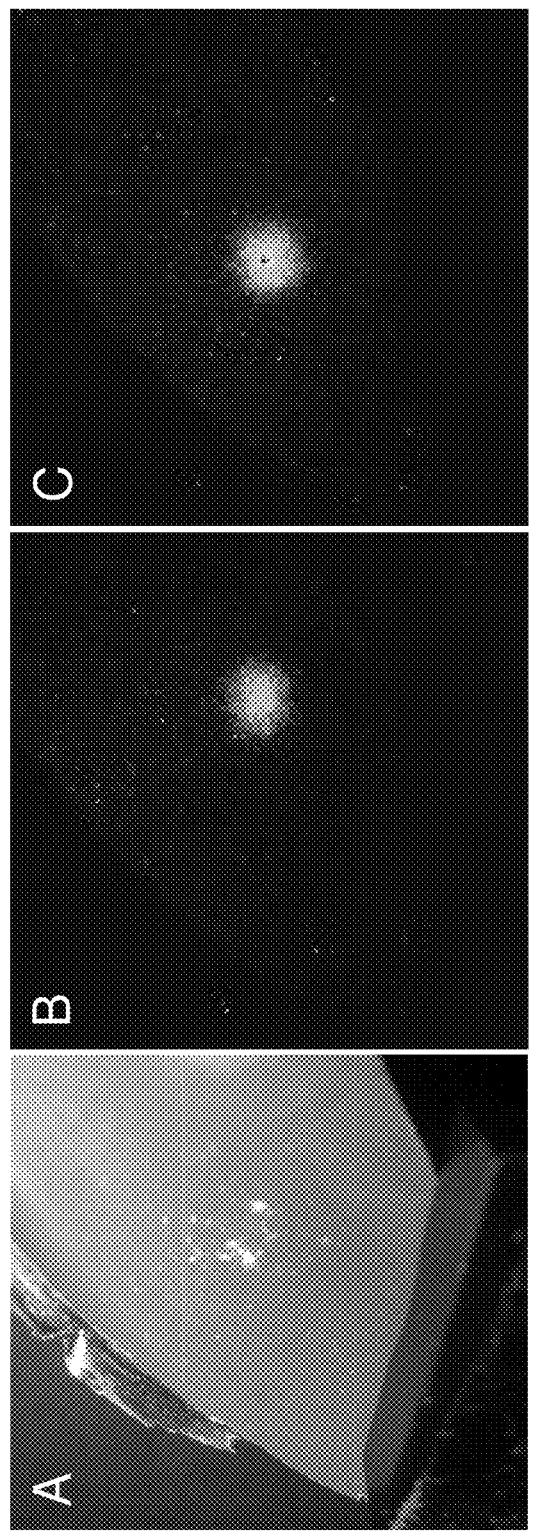
FIG. 16 (A) shows an image of an automobile taken with an ordinary (visible wavelength) camera.

As an example of the imaging capability, traces of the explosive RDX were deposited onto a plate cut from an automobile. FIG. 16 (A) shows an image of the automobile taken with an ordinary (visible wavelength) camera. FIG. 16 (B) is a (LWIR) infrared camera image showing that the heating effect of the laser (light area) is minimal where no RDX is present. In FIG. 16 (C), where RDX is present, the thermal image clearly reveals the heating due to the laser (dark dot within the light area). Both images (B) and (C) are frames from a movie where the laser beam is scanned across wide areas of the sample surface.

Example 7

Figure 17:
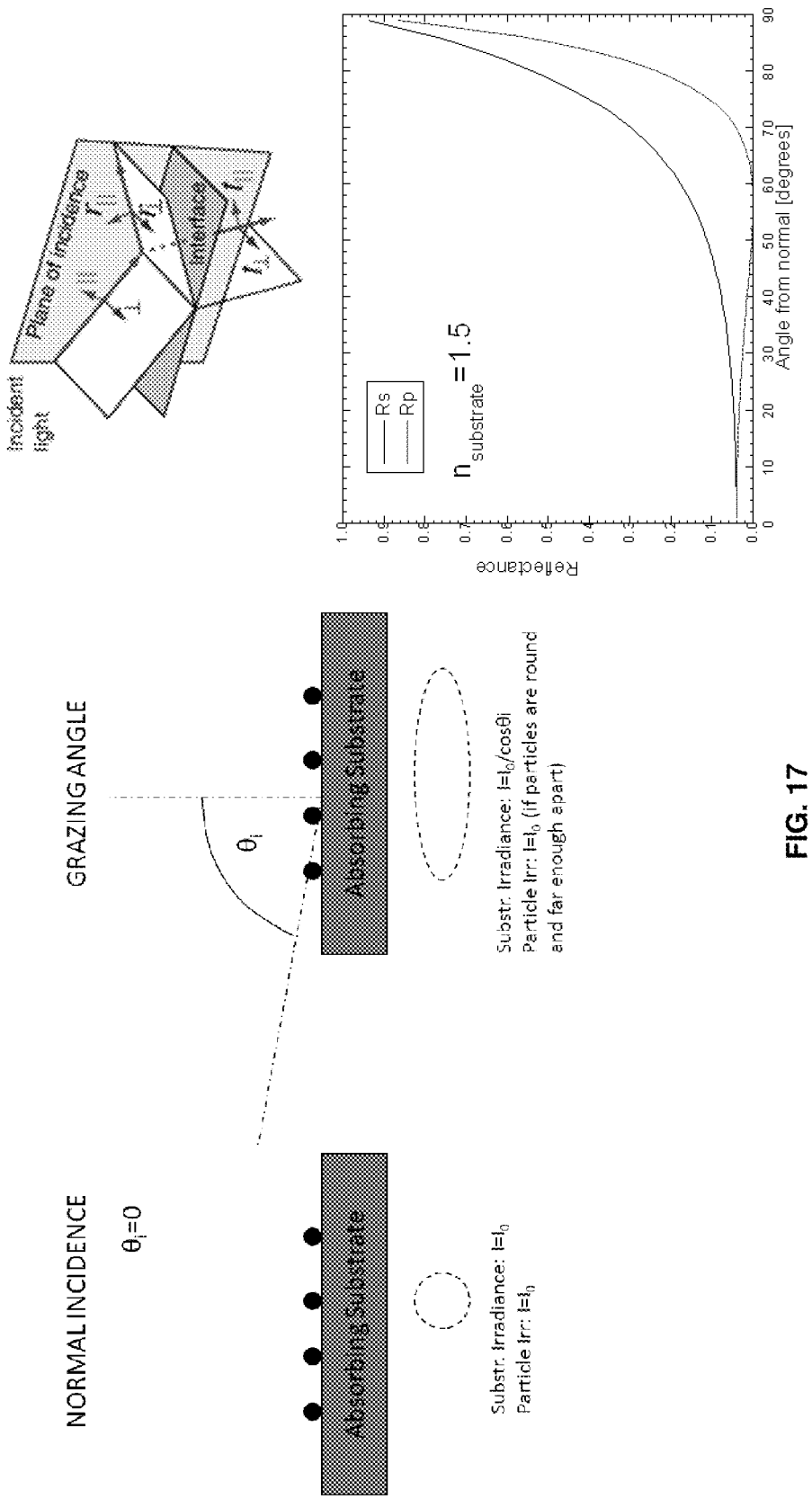
FIG. 17 shows the IR light source at a small (i.e. grazing) angle with respect to the substrate.
Figure 18:
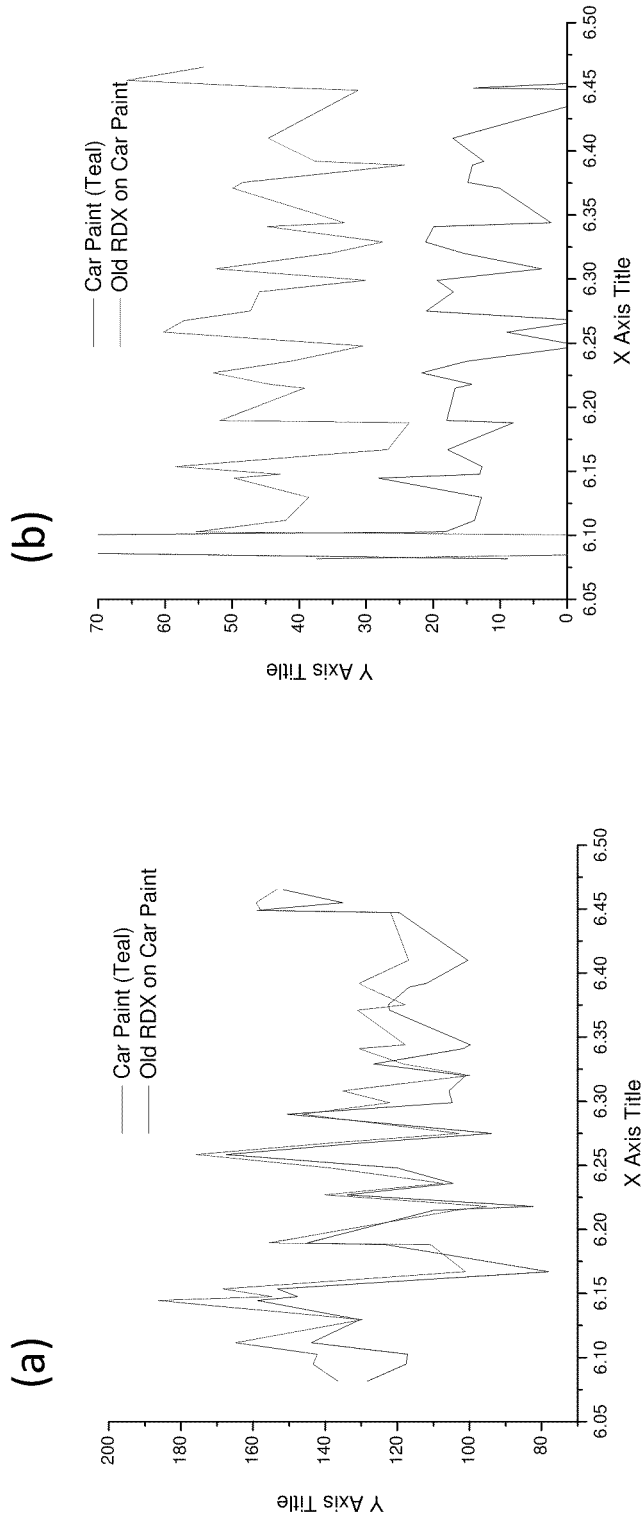
FIG. 18 shows an example of RDX powder on a car panel.

Further reduction of the influence of the substrate on the signal can be achieved by performing the measurement in such a way that the IR light source is at a small (i.e. grazing) angle with respect to the substrate. This has two advantages. First, it spreads the beam over a larger area and thus reduces substrate heating while at the same time particles receive approximately the same energy due to their round shape. Second, the reflectance coefficient of the substrate will increase and less light gets absorbed. This effect is even more pronounced if the polarization of the IR light is aligned with the substrate in such a way that the electric field of the excitation is parallel to the substrate surface. FIG. 17 illustrates this concept. FIG. 18 shows an example of RDX powder on a car panel. At normal incidence there is no difference observed between the RDX on the car panel sample and the pure car panel only. At grazing incidence, there is four times more signal from the RDX than from the car panel. Note that this experiment was not done in the chopping (modulated) modality and therefore the spectral content is absent.

Example 8

Figure 19:
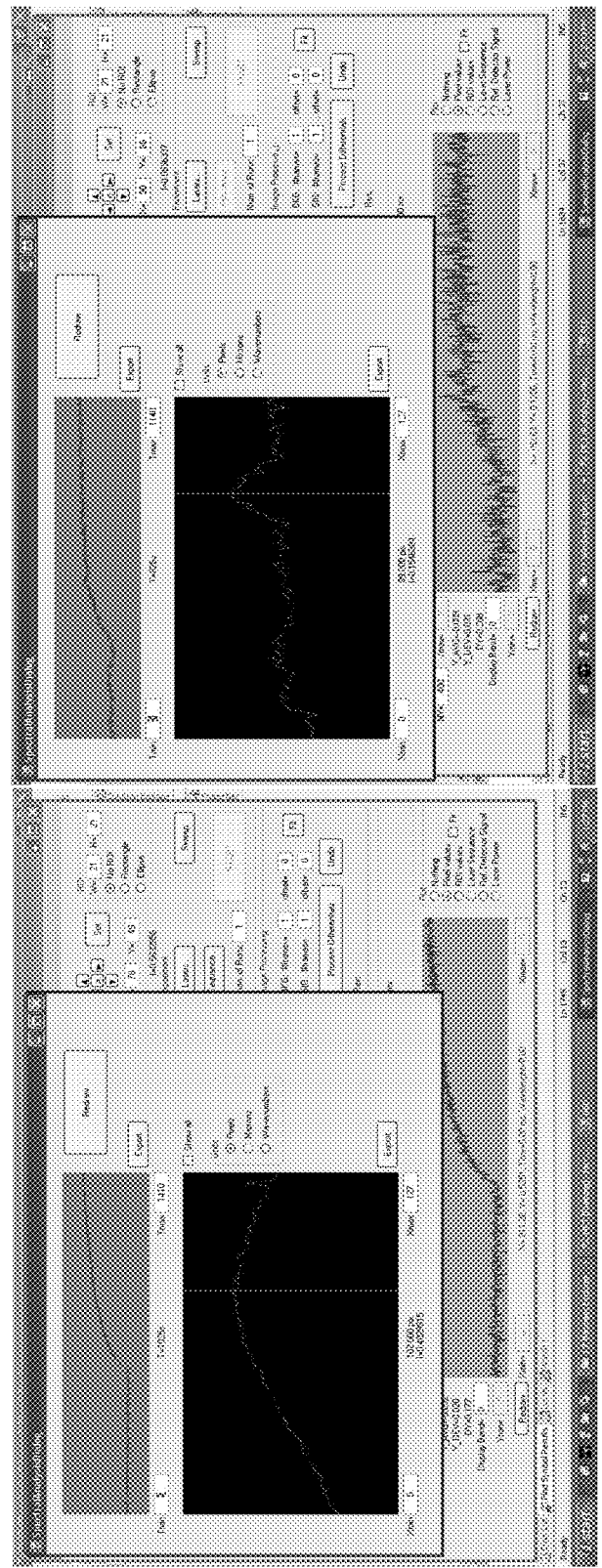
FIG. 19 shows the emission spectrum of a blackbody source compared to DNT on a polyethylene substrate illuminated by a 7.4 micron laser.

By spectrally resolving the emission signal, it is possible to improve detection selectivity because the emission signal has a distinct spectrum. FIG. 19 shows the emission spectrum of a blackbody source compared to DNT on a polyethylene substrate illuminated by a 7.4 micron laser. The emission is in the 8-10 micron region for both samples. The DNT spectrum has peaks characteristic of DNT absorption in this region while the blackbody spectrum is smooth across the band. The emission was spectrally resolved by imaging the emission from a single point on the sample through an IR monochromator onto a 128×128 cooled MCT array.

Example 9

Figure 20:
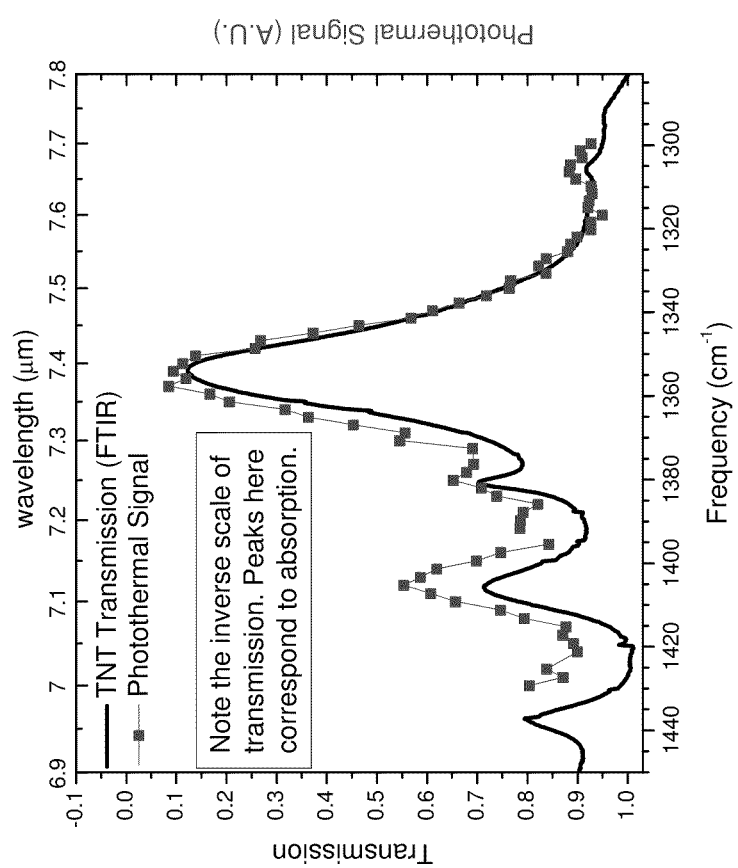
FIG. 20 shows an example of stand-off tunable photo-thermal spectroscopy of TNT.

FIG. 20 shows an example of stand-off tunable photo-thermal spectroscopy of TNT. The FTIR transmission of TNT (thick black line) is compared with the photo-thermal signal (thin line with filled box data points) measured at 0.5 meter stand-off. A tunable QCL was stepped in increments of 0.01 μm from 7.0 to 7.7 μm (71 points). The photo-thermal axis scaling is arbitrary and is normalized here for comparison with the FTIR spectrum. The overall agreement is good, with each of the five distinct TNT absorption bands being faithfully observed in the PT measurements.

Example 10

Figure 21:
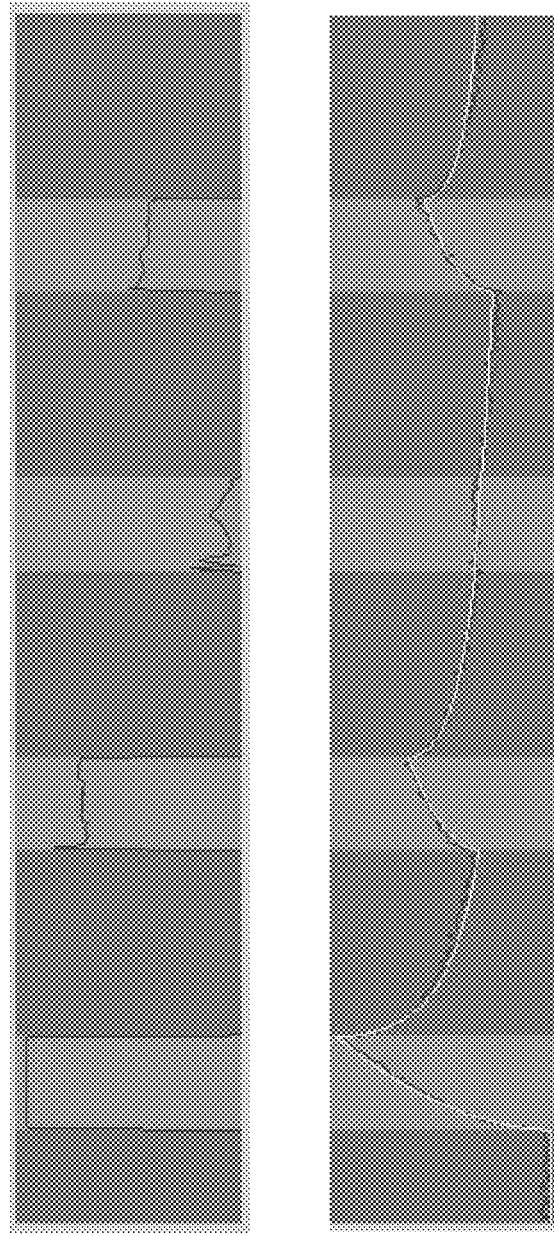
FIG. 21 shows an example of fitting the signal to a function obtained by convolving the laser power output with the impulse response of the system.

For short measurement of samples that have a long cooling time, the cooling does not finish before the next laser pulse begins. This will cause the signals to overlap and cause problems in interpreting the data. To decouple the effects of previous laser pulses on subsequent pulses, the signal can be fitted to a function obtained by convolving the laser power output with the impulse response of the system. FIG. 21 shows an example of this fitting procedure.

Example 11

Figure 22:
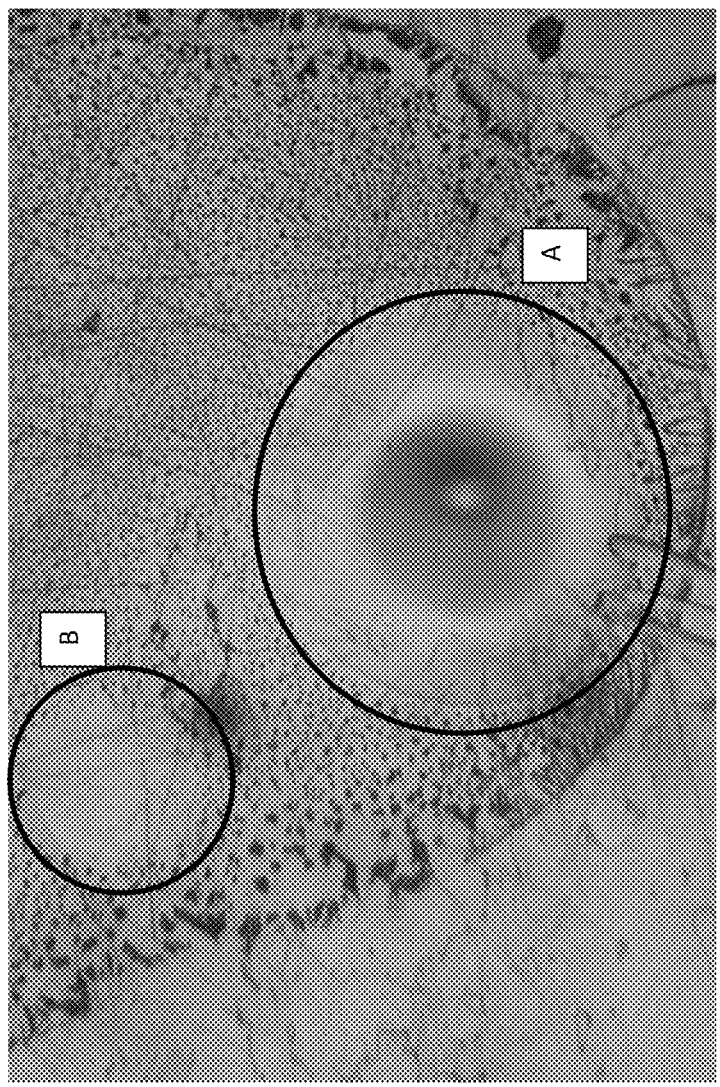
FIG. 22 shows particles of an explosive material dried from a solution deposit on a substrate. The large circle in the lower center of the image (A) shows a portion of the analyte-coated substrate which has been exposed for 2 seconds to an infrared laser. The substrate has been melted over a region larger than the beam diameter. The circle above and to the left (B) shows the sample after exposure to the same laser intensity for two seconds but with a mechanical chopper that interrupted the laser beam at 100 Hz and at a 40% duty cycle. In this instance the deposited material has been completely vaporized while the substrate remains unaltered. The diameter of Circle B is about 500 microns.

FIG. 22 shows particles of an explosive material dried from a solution deposit on a substrate. The large circle in the lower center of the image (A) shows a portion of the analyte-coated substrate which has been exposed for 2 seconds to an infrared laser. The substrate has been melted over a region larger than the beam diameter. The circle above and to the left (B) shows the sample after exposure to the same laser intensity for two seconds but with a mechanical chopper that interrupted the laser beam at 100 Hz and at a 40% duty cycle. In this instance the deposited material has been completely vaporized while the substrate remains unaltered. The diameter of Circle B is about 500 microns.

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," are not to be construed as limiting the element to the singular.

What is claimed as new and desired to be protected by Letters Patent of the United States is:

1. A method for non-contact analyte detection, comprising:
   (a) selectively exciting one or more condensed phase analytes of interest on a substrate using an IR source that is optionally operated to produce pulses of light and tuned to at least one specific absorption band without decomposing more than five percent of organic analytes; and
   (b) determining if the analyte is present by comparing emitted photons from the analyte present on the substrate with an IR detector signal collected one or more times before, during, after, or any combination thereof exciting the analyte.

2. The method of claim 1, wherein the emitted photons are produced at one or more wavelengths by photo-thermal transduction.

3. The method of claim 1, additionally comprising analyzing at least one other optical or non-optical signal.

4. The method of claim 1, additionally comprising analyzing at least one other signal selected from the group consisting of reflectivity, emissivity, scattering, fluorescence, luminescence, Raman scattering, LIDAR, and photo-acoustic emission.

5. The method of claim 1, wherein the different times of the signal, a time dependence of the signal, or both is used in combination with a spectral signature.

6. The method of claim 1, wherein one or more excitation sources are used with one or more optical collection filters.

7. The method of claim 6, wherein at least one excitation source or one optical collection filter is tunable.

8. The method of claim 1, wherein the collected photons are optionally spectrally dispersed.

9. The method of claim 1, wherein an array detector may be used to generate a spatially resolved image of the emitted signal.

10. The method of claim 1, wherein spectral signals, spatial signals, different times of the signals, a time dependence of the signals, or any combination thereof are considered.

11. The method of claim 1, wherein the analyte is on any body part including hair and nails.

12. The method of claim 1, wherein the analyte is on a piece of apparel, footwear, or accessory.

13. The method of claim 1, wherein the analyte is in or on a package, baggage, a document, an electronic device, a building part, a vehicle part, or a drug.

14. The method of claim 1, wherein the analyte is harvested to a substrate.

15. The method of claim 1, wherein prior to excitation, the analyte is collected via an analyte collecting device, a portal system, a vacuum device, contact-swabbing a surface, or any combination thereof.

16. The method of claim 1, wherein malfunctioning detector pixels are identified and managed.

17. The method of claim 1, wherein multiple illumination pulses are used in sequence.

18. The method of claim 1, wherein stand-off analysis is performed by using a lens or a parabolic reflector to direct the collected light towards an infrared detector or an optical fiber.

19. The method of claim 1, wherein the analyte is on a substrate and the excitation is directed at a grazing angle with respect to the substrate and optionally the electric field of the IR source is parallel to the substrate.

20. The method of claim 1, wherein the analyte is on a substrate and the excitation is moved with respect to the substrate.

21. A method for non-contact analyte detection, comprising:
   (a) selectively exciting one or more analytes of interest using an IR source that is optionally operated to produce pulses of light and tuned to at least one specific absorption band without decomposing more than five percent of organic analytes; and
   (b) determining if the analyte is present by comparing emitted photons with an IR detector signal collected one or more times before, during, after, or any combination thereof exciting the analyte; and
   additionally comprising applying a prior cuing technique, surveying technique, or both.

22. The method of claim 21, wherein the cuing or surveying technique may comprise IR light, passive or active reflectivity, emissivity, scattering, fluorescence, luminescence, Raman scattering, LIDAR, photo-acoustic emission, or any combination thereof.

23. The method of claim 1, A method for non-contact analyte detection, comprising:
   (a) selectively exciting one or more analytes of interest using an IR source that is optionally operated to produce pulses of light and tuned to at least one specific absorption band without decomposing more than five percent of organic analytes; and
   (b) determining if the analyte is present by comparing emitted photons with an IR detector signal collected one or more times before, during, after, or any combination thereof exciting the analyte; and
   wherein a time dependence of the signal is used to distinguish emissions from the analyte and emissions from a substrate at least partially covered by the analyte.

24. The method of claim 1, A method for non-contact analyte detection, comprising:
   (a) selectively exciting one or more analytes of interest using an IR source that is optionally operated to produce pulses of light and tuned to at least one specific absorption band without decomposing more than five percent of organic analytes; and
   (b) determining if the analyte is present by comparing emitted photons with an IR detector signal collected one or more times before, during, after, or any combination thereof exciting the analyte; and
   wherein the different times of the signal, a time dependence of the signal, or both is used to distinguish faster emission phenomena from slower emission phenomena.

25. The method of claim 24, wherein faster emission phenomena may comprise reflection, elastic backscattering, Raman scattering, or any combination thereof, and wherein slower emission phenomena may comprise photo-thermal, photoluminescence, fluorescence, or any combination thereof.

26. A method for non-contact analyte detection, comprising:
(a) selectively exciting one or more analytes of interest using an IR source that is optionally operated to produce pulses of light and tuned to at least one specific absorption band without decomposing more than five percent of organic analytes; and
(b) determining if the analyte is present by comparing emitted photons with an IR detector signal collected one or more times before, during, after, or any combination thereof exciting the analyte; and
wherein individual pixels in the same spatially resolved image are compared to determine inhomogeneous responses.

27. A method for non-contact analyte detection, comprising selectively exciting one or more condensed phase ionically bonded analytes of interest on a substrate using one or more IR sources that are optionally operated to produce pulses of light and tuned to at least one specific wavelength, wherein the analyte is excited sufficiently to increase the concentration of analyte for gas phase analysis, and wherein the content of the gas phase is examined to determine the presence of the analyte.

28. The method of claim 27, wherein multiple IR wavelengths are used simultaneously or in sequence.

29. The method of claim 27, wherein the analyte is on any human body part including hair and nails.

30. The method of claim 27, wherein the analyte is on a piece of apparel, footwear, or accessory.

31. The method of claim 27, wherein the analyte is in or on a package, baggage, a document, an electronic device, a building part, a vehicle part, or a drug.

32. The method of claim 27, wherein one or more excitation sources are applied in two or more steps.

33. The method of claim 27, wherein the gas is sampled and directed to a gas chromatography (GC) column.

34. The method of claim 27, wherein the analyte is on a substrate and the excitation is directed at a grazing angle with respect to the substrate and optionally the electric field of the IR source is parallel to the substrate.

35. A method for non-contact analyte detection, comprising selectively exciting one or more analytes of interest using one or more IR sources that are optionally operated to produce pulses of light and tuned to at least one specific wavelength without decomposing more than five percent of organic analytes, wherein the analyte is excited sufficiently to increase the amount of analyte in the gas phase, wherein the content of the gas is examined to detect the presence of the analyte, wherein one or more excitation sources are applied in two or more steps, and wherein the initial pulses are used to remove a surface layer of water or other volatile chemicals to leave behind a surface with the analyte of interest which is then targeted with subsequent pulses of light.

36. A method for non-contact analyte detection, comprising selectively exciting one or more analytes of interest using one or more IR sources that are optionally operated to produce pulses of light and tuned to at least one specific wavelength without decomposing more than five percent of organic analytes, wherein the analyte is excited sufficiently to increase the amount of analyte in the gas phase, wherein the content of the gas is examined to detect the presence of the analyte, wherein the gas is sampled and directed to a gas chromatography (GC) column, and wherein the analyte is trapped in a sorbent coated inlet region of the GC column and released by heating with infrared light that enters the GC column and is incident on the sorbent coated trapping region.

37. A method for non-contact analyte detection, comprising selectively exciting one or more analytes of interest using one or more IR sources that are optionally operated to produce pulses of light and tuned to at least one specific wavelength without decomposing more than five percent of organic analytes, wherein the analyte is excited sufficiently to increase the amount of analyte in the gas phase, wherein the content of the gas is examined to detect the presence of the analyte, wherein the gas is sampled and directed to a gas chromatography (GC) column, and wherein the analyte is trapped in a sorbent coated inlet region of the GC column and released by heating with infrared light that passes through an IR transparent column material or window and onto the sorbent coated trapping region.

38. A method for non-contact analyte detection, comprising selectively exciting one or more analytes of interest using one or more IR sources that are optionally operated to produce pulses of light and tuned to at least one specific wavelength without decomposing more than five percent of organic analytes, wherein the analyte is excited sufficiently to increase the amount of analyte in the gas phase, and wherein the content of the gas is examined to detect the presence of the analyte, and wherein the gas is collected for subsequent analysis.

39. A method for non-contact analyte detection, comprising selectively exciting one or more analytes of interest using one or more IR sources that are optionally operated to produce pulses of light and tuned to at least one specific wavelength without decomposing more than five percent of organic analytes, wherein the analyte is excited sufficiently to increase the amount of analyte in the gas phase, and wherein the content of the gas is examined to detect the presence of the analyte, and wherein the gas is collected to a preconcentrator and subsequently desorbed into an analytical system.

40. A method for non-contact analyte detection, comprising selectively exciting one or more analytes of interest using one or more IR sources that are optionally operated to produce pulses of light and tuned to at least one specific wavelength without decomposing more than five percent of organic analytes, wherein the analyte is excited sufficiently to increase the amount of analyte in the gas phase, and wherein the content of the gas is examined to detect the presence of the analyte, and wherein the gas is collected to a suitable substrate and the method of claim 1 is performed.

41. A method for non-contact analyte detection, comprising selectively exciting one or more analytes of interest using one or more IR sources that are optionally operated to produce pulses of light and tuned to at least one specific wavelength without decomposing more than five percent of organic analytes, wherein the analyte is excited sufficiently to increase the amount of analyte in the gas phase, and wherein the content of the gas is examined to detect the presence of the analyte, and wherein the gas is collected to a Surface Enhanced Raman Scattering (SERS) substrate and analyzed.

42. A method for non-contact analyte detection, comprising selectively exciting one or more analytes of interest using one or more IR sources that are optionally operated to produce pulses of light and tuned to at least one specific wavelength without decomposing more than five percent of organic analytes, wherein the analyte is excited sufficiently to increase the amount of analyte in the gas phase, and wherein the content of the gas is examined to detect the presence of the analyte, and wherein the gas is collected to a surface suitable for spectroscopic identification.

43. A method for non-contact analyte detection, comprising selectively exciting one or more analytes of interest using one or more IR sources that are optionally operated to produce pulses of light and tuned to at least one specific wavelength without decomposing more than five percent of organic analytes, wherein the analyte is excited sufficiently to increase the amount of analyte in the gas phase, and wherein the content of the gas is examined to detect the presence of the analyte, and wherein gaseous analyte is drawn into a cone or funnel that is optionally heated then directed into a preconcentrator.

44. A method for non-contact analyte detection, comprising selectively exciting one or more analytes of interest using one or more IR sources that are optionally operated to produce pulses of light and tuned to at least one specific wavelength without decomposing more than five percent of organic analytes, wherein the analyte is excited sufficiently to increase the amount of analyte in the gas phase, and wherein the content of the gas is examined to detect the presence of the analyte, and
  wherein an analyte on a solid surface is released into the air by heating with an infrared source, the released analyte is drawn to a preconcentrator to collect analytes of interest, the preconcentrator is subsequently heated to direct the released analyte into an analytical system which optionally comprises a gas chromatograph, and the released analyte exiting the analytical system may enter a gas cell where the analyte is monitored and detected by using an infrared laser to excite the analyte and examining if light is produced.

45. A method for non-contact analyte detection, comprising selectively exciting one or more analytes of interest using one or more IR sources that are optionally operated to produce pulses of light and tuned to at least one specific wavelength without decomposing more than five percent of organic analytes, wherein the analyte is excited sufficiently to increase the amount of analyte in the gas phase, and wherein the content of the gas is examined to detect the presence of the analyte, wherein the IR source delivers a finite number of pulses and wherein the substrate temperature is optionally monitored.

* * * * *